(12) United States Patent
Fritchie et al.

(10) Patent No.: US 7,688,207 B2
(45) Date of Patent: Mar. 30, 2010

(54) SYSTEM FOR TRACKING VESSELS IN AUTOMATED LABORATORY ANALYZERS BY RADIO FREQUENCY IDENTIFICATION

(75) Inventors: Patrick P. Fritchie, Southlake, TX (US); Gregory E. Gardner, Grapevine, TX (US); Richard W. Mahoney, Grapevine, TX (US); Oscar F. Schwartz, Arlington, TX (US)

(73) Assignee: Abbott Laboratories Inc., Abbott Park, IL (US)

( * ) Notice: Subject to any disclaimer, the term of this patent is extended or adjusted under 35 U.S.C. 154(b) by 221 days.

(21) Appl. No.: 11/495,430

(22) Filed: Jul. 28, 2006

(65) Prior Publication Data

US 2008/0024301 A1    Jan. 31, 2008

(51) Int. Cl.
*G08B 13/14* (2006.01)

(52) U.S. Cl. ............... 340/572.1; 340/10.1; 340/539.1; 340/568.1

(58) Field of Classification Search ... 340/572.1–572.9, 340/10.1, 539.1, 539.11, 539.13, 5.1, 5.2, 340/5.61, 5.8, 825.36, 568.1; 235/439, 454, 235/462.01, 462.13

See application file for complete search history.

(56) References Cited

U.S. PATENT DOCUMENTS

| | | | |
|---|---|---|---|
| 4,673,932 A | 6/1987 | Ekchian et al. | |
| 4,941,201 A | 7/1990 | Davis | |
| 5,096,670 A | 3/1992 | Harris et al. | |
| 5,122,342 A | 6/1992 | McCulloch et al. | |
| 5,406,263 A | 4/1995 | Tuttle | |
| 5,771,657 A | 6/1998 | Lasher et al. | |
| 5,856,788 A * | 1/1999 | Walter et al. | 340/10.2 |
| 5,963,136 A | 10/1999 | O'Brien | |
| 6,107,920 A | 8/2000 | Eberhardt et al. | |
| 6,146,882 A * | 11/2000 | Uematsu et al. | 435/303.1 |
| 6,294,999 B1 | 9/2001 | Yarin et al. | |
| 6,343,690 B1 | 2/2002 | Britton et al. | |
| 6,359,444 B1 | 3/2002 | Grimes | |
| 6,535,129 B1 | 3/2003 | Petrick | |
| 6,540,965 B2 | 4/2003 | Bara | |
| 6,599,476 B1 * | 7/2003 | Watson et al. | 422/63 |
| 6,600,418 B2 * | 7/2003 | Francis et al. | 340/572.1 |

(Continued)

FOREIGN PATENT DOCUMENTS

EP    1 339 032 A2    8/2003

(Continued)

OTHER PUBLICATIONS

Der 2006-410013, May 2005, Derwent, Kwon.*

(Continued)

*Primary Examiner*—Daniel Previl
(74) *Attorney, Agent, or Firm*—David L. Weinstein (57) ABSTRACT

A system for automation of laboratory analyzers that utilizes radio frequency identification (RFID) tags and radio frequency identification (RFID) readers to identify containers and vessels, and the contents thereof, that are employed in the system. Radio frequency identification tags, conforming to the guidelines of ISO 14443 or ISO 15693 or ISO 18000, are positioned on the items of interest, such as, for example, reagent containers, sample containers, and microplates. These tags can be read by and written to by either a moving antenna of a RFID reader or a stationary antenna of a RFID reader. Reading of RFID tags and writing to RFID tags are controlled by software.

45 Claims, 6 Drawing Sheets

U.S. PATENT DOCUMENTS

| | | |
|---|---|---|
| 6,677,857 B2 | 1/2004 | Bara et al. |
| 6,847,912 B2 | 1/2005 | Forster |
| 6,879,876 B2 | 4/2005 | O'Dougherty et al. |
| 6,968,876 B2* | 11/2005 | Yacko et al. ............... 141/361 |
| 7,019,639 B2* | 3/2006 | Stilp ........................... 340/531 |
| 7,070,053 B1* | 7/2006 | Abrams et al. ........... 206/459.5 |
| 7,175,334 B2* | 2/2007 | Babson et al. ............... 366/109 |
| 7,178,416 B2 | 2/2007 | Whelan et al. |
| 7,250,845 B2* | 7/2007 | Young et al. ............... 340/5.92 |
| 7,275,682 B2 | 10/2007 | Excoffier et al. |
| 7,277,015 B1* | 10/2007 | Morhard et al. ........... 340/572.1 |
| 7,342,497 B2* | 3/2008 | Chung et al. .............. 340/572.1 |
| 2003/0174046 A1 | 9/2003 | Abrams |
| 2003/0183683 A1 | 10/2003 | Stewart |
| 2004/0036626 A1 | 2/2004 | Chan et al. |
| 2004/0258565 A1 | 12/2004 | Watari |
| 2004/0265187 A1 | 12/2004 | Davin |
| 2005/0009122 A1 | 1/2005 | Whelan et al. |
| 2005/0019943 A1* | 1/2005 | Chaoui et al. ............... 436/165 |
| 2005/0036907 A1 | 2/2005 | Shoji |
| 2005/0106747 A1 | 5/2005 | Chaoui et al. |
| 2005/0177274 A1 | 8/2005 | O'Dougherty et al. |
| 2005/0186114 A1 | 8/2005 | Reinhardt et al. |
| 2005/0205673 A1* | 9/2005 | Morris et al. ............... 235/385 |
| 2005/0242963 A1 | 11/2005 | Oldham et al. |
| 2005/0248455 A1 | 11/2005 | Pope et al. |
| 2006/0018996 A1* | 1/2006 | Pollock et al. ................. 426/19 |
| 2006/0213964 A1 | 9/2006 | Excoffier |
| 2006/0245865 A1* | 11/2006 | Babson .................. 414/331.01 |
| 2007/0036686 A1 | 2/2007 | Hatamian et al. |
| 2007/0040682 A1* | 2/2007 | Zhu et al. ................. 340/572.1 |
| 2007/0080804 A1* | 4/2007 | Hirahara et al. ........... 340/572.1 |
| 2007/0120685 A1 | 5/2007 | Morris et al. |
| 2007/0255756 A1 | 11/2007 | Satomura et al. |
| 2008/0063563 A1 | 3/2008 | Watari |

FOREIGN PATENT DOCUMENTS

| | | |
|---|---|---|
| EP | 1 339 032 A3 | 1/2004 |
| EP | 1 374 987 A1 | 1/2004 |
| EP | 1867998 A2 | 12/2007 |
| GB | 2 308 947 A | 7/1997 |
| JP | 2004028595 | 1/2004 |
| JP | 2004093518 | 3/2004 |
| JP | 2004093519 | 3/2004 |
| WO | 2001056753 A1 | 8/2001 |
| WO | WO 01/94016 A1 | 12/2001 |
| WO | WO 02/48955 A1 | 6/2002 |
| WO | WO 02/101670 A2 | 12/2002 |
| WO | WO 03/044521 A1 | 5/2003 |
| WO | WO 2004/008387 A1 | 1/2004 |
| WO | WO 2004/044824 A2 | 5/2004 |
| WO | WO 2004/044824 A3 | 5/2004 |
| WO | WO 2004/081746 A2 | 9/2004 |
| WO | WO 2004/081746 A3 | 9/2004 |
| WO | WO 2005/024385 A2 | 3/2005 |
| WO | WO 2005/028110 A2 | 3/2005 |
| WO | WO 2005/028110 A3 | 3/2005 |
| WO | 2005098455 A1 | 10/2005 |
| WO | 2005109332 A1 | 11/2005 |
| WO | WO 2005/110600 A2 | 11/2005 |
| WO | 2006060125 A2 | 6/2006 |
| WO | 2007024540 A1 | 3/2007 |

OTHER PUBLICATIONS

Notification of Transmittal of the International Search Report and the Written Opinion of the Interantional Searching Authority, or the Declaration, European Patent Office, May 14, 2008.

* cited by examiner

SYSTEM FOR TRACKING VESSELS IN AUTOMATED LABORATORY ANALYZERS BY RADIO FREQUENCY IDENTIFICATION

BACKGROUND OF THE INVENTION

1. Field of the Invention

This invention relates to systems that utilize automated laboratory analyzers, and more particularly, systems that utilize automated laboratory analyzers that require identification of containers for biological samples and reagents.

2. Discussion of the Art

Previous implementations for identification of reagents and other consumable items for automated laboratory analyzers have utilized barcode technology. Barcodes have been attached to items of interest, such as, for example, reagent containers, sample containers, e.g., test tubes, and test tube racks, and selectively scanned by a barcode reader for the purpose of identification and tracking of information associated with these items.

Barcode technology has several limitations that inhibit optimally efficient architectures of automated analyzers for use in laboratories. Reading barcodes requires a direct line-of-sight from the barcode reader to the barcode. In addition, the barcode typically occupies a large portion of the surface of a reagent container or test tube. Because the barcode occupies such a large surface area, the reagent containers and the sample containers must be separated by a great distance, and, consequently, the reagent containers and the sample containers consume a large area of the analyzer. Another adverse effect of the use of a large area of the analyzer is that the range of motion for aspirating devices, such as, for example, pipettes, and refrigeration equipment must be greatly increased. Still another adverse effect of barcode technology is that barcode readers of increasing complexity must be used because the barcode readers require variable depths of field. The sizes of barcodes and the surfaces of the reagent containers and sample containers limit the amount of data that can be associated with the containers. Barcodes cannot be updated to account for changes in the amount of reagent or sample, i.e., the number of tests remaining, or the on-board expiration date of the reagent after the reagent container has been opened. Furthermore, cleaning and alignment of barcode reader windows account for about half of the barcode reading problems reported in the field.

Radio frequency identification (hereinafter alternatively referred to as "RFID") technology can be used as a replacement for barcodes and barcode readers in order to promote more efficient architectures for analyzers. RFID tags can be placed on a small portion of the surface of a reagent container and read in close proximity to a RFID reader, thereby minimizing the area required of the analyzer, and further minimizing the range of motion required for aspirating devices, e.g., pipettes, and refrigeration equipment. RFID tags typically utilize silicon-based memory chips, which can contain many times more information than can barcodes. RFID tags can be written to and can be updated with information relating to the analyzer, the environment, and the reagent container, thereby providing improved functioning of the analyzer, improved chain of custody, and improved safety to consumers. RFID tags can be read in a wide range of environmental conditions, with the result that cleaning and alignment of barcodes are not required.

There have been some attempts to utilize RFID tags in the environment of automated laboratory analyzers. See, for example, U.S. Pat. No. 6,879,876; U.S. Patent Application Publication No. 2004/0258565; U.S. Patent Application Publication No. 2005/0019943; U.S. Patent Application Publication No. 2005/0036907; U.S. Patent Application Publication No. 2005/0106747; U.S. Patent Application Publication No. 2005/0186114; WO 2004/044824; and WO 2005/024385.

There is a desire for a system for updating data relating to samples and reagents. There is a desire for a system that enables movement of a reagent from one automated system to another in the case of the failure of an automated system. There is a desire for an automated system that enables the updating of the demographics of patients, whereby the results of the assays of numerous biological samples can be correlated with various statistics associated with those patients providing the biological samples.

SUMMARY OF THE INVENTION

This invention provides a system for automation of laboratory analyzers that utilizes radio frequency identification (RFID) tags and radio frequency identification (RFID) readers to identify containers and vessels, and the contents thereof, that are employed in the system. Radio frequency identification tags, conforming to the guidelines of ISO 14443 or ISO 15693 or ISO 18000, are positioned on the items of interest, such as, for example, reagent containers, sample containers, and microplates. These tags can be read by and written to by either a moving antenna of a RFID reader or a stationary antenna of a RFID reader. Reading of RFID tags and writing to RFID tags are controlled by software.

In one aspect, the system of this invention comprises a plurality of containers, each of which has a radio frequency identification tag attached thereto at a suitable position thereon. In one embodiment, the system includes at least one movable radio frequency identification reader. In order for the radio frequency identification reader to read the data from the radio frequency identification tag associated with a container, the reader is caused to move to a position proximate to the radio frequency identification tag so that the information from the tag can be read with an amount of noise and interference from nearby radio frequency identification tags on other containers that are insufficient to adversely affect the integrity of the data read by a RFID reader. In this embodiment, a transmission sub-system must be provided to enable the at least one RFID reader to move among the containers.

In another embodiment, the system includes at least one stationary radio frequency identification reader. In order for the at least one radio frequency identification reader to read the data from the radio frequency identification tag associated with a container, the container is caused to move to a position proximate to, and preferably in register with, the at least one radio frequency identification reader so that the information from the tag can be read with an amount of noise and interference from nearby radio frequency identification tags on other containers that are insufficient to adversely affect the integrity of the data read by a RFID reader. In this embodiment, a transmission sub-system need not be provided to enable the at least one reader to move among the containers.

There are at least two ways to implement the foregoing embodiment. According to a first way, containers for samples and containers for reagents can be transported to a position proximate to at least one RFID reader, whereby RFID tags on the containers can be read by the at least one RFID reader. According to a second way, each antenna, which is a trace on a printed circuit board, functions as a separate antenna for a RFID-reader. In other words, the RFID-reader has a plurality of channels, each channel having a separate antenna. The length of the antenna is important, because the length determines the relationship with the radio frequency used. The length of the antenna corresponds to some multiple of wavelength of radio frequency energy, e.g., one-half wavelength, one-quarter wavelength.

In order to implement the system of this invention, a radio frequency identification tag can be positioned on the lowermost portion of a container. It is often desirable to position an encapsulated radio frequency identification tag on the lowermost portion of a container.

In another aspect, a method is provided whereby the system previously described can read the data from radio frequency identification tags attached to containers.

The system described herein provides the ability to aggregate read information with a container in addition to the sample identifier or the reagent identifier. For sample containers, read information, other than the sample identifier, can include (a) demographics of patients, (b) the date the sample was obtained, (c) the test(s) to be performed upon the sample, (d) the type of sample, (e) the type of container, etc. The system provides the ability to track shipping and storage conditions that may affect the integrity of a biological sample. In addition, the system can be used for writing information, such as, for example, centrifugation operations performed, aspiration operations performed, potential contamination or dilution of a sample by material carried over by the tip of an aspirating device, temperature conditions of the sample, freeze-thaw conditions of the sample, etc.

For reagent containers, read information, other than the reagent identifier, can include (a) calibration data for the reagent, (b) lot number of the reagent, (c) serial number of the reagent, (d) identification of components of the reagent, (e) identification of the assay, (f) expiration date of the reagent, (g) kit size, (h) package insert information, etc. The system provides the ability to track shipping and storage conditions that may affect integrity of a reagent. In addition, the system can be used for writing information such as (a) tests remaining, (b) on-board expiration date (after the container has been opened), (c) aspiration operations performed, and (d) potential contamination or dilution of samples and reagents by material carried over by the tip of an aspirating device, etc.

For microplates, read information, other than the microplate identifier, can include (a) manufacturing lot number of a microplate, (b) serial number of a microplate, (c) expiration date of the reagent(s) in the microplate, etc. The system provides the ability to track shipping and storage conditions that may affect integrity of the microplate. In addition, the system can be used for writing information such as (a) date used, (b) on-board expiration of the microplate (after the microplate has been opened), etc.

The use of a RFID system allows a more compact physical architecture than would be possible with barcode technology by eliminating line of sight and spatial separation requirements, (b) improving reliability (in extreme environments) of reading information on a container, vessel, and microplate.

The use of a RFID system also enables proper physical orientation of containers, i.e., the system ensures that a given container, vessel, microplate is in the proper location prior to its use.

Radio frequency identification can be used to increase the quantity of information on the container, the vessel, or the microplate. In addition, a radio frequency identification tag can be updated; a barcode cannot be updated. Furthermore, the information can be directly linked to a database, thereby providing (a) improved functioning of automated analyzer(s) in a system, (b) improved chain of custody, i.e., improved information relating to locations occupied by a given container in the present and at times previous to the present, and (c) improved safety to patients by ensuring accurate results of assays. This information includes information relating to the analyzer, the environment, i.e., the environments experienced during shipping, storage, and usage of the contents of the container.

The system also provides the ability to positively verify a sample or identify a reagent during aspiration or dispensing, thereby enabling an operator of the system to be given physical access to samples and reagents, except for those samples and reagents currently being aspirated or dispensed. Physical access to samples or reagents currently being aspirated or dispensed should be prohibited to the operator in order to ensure the safety of the operator.

DETAILED DESCRIPTION

As used herein, the expression "radio frequency identification", or RFID, is a generic term for technologies that use radio waves to automatically identify objects, such as, for example, containers for biological samples and containers for reagents for analyzing biological samples. The most common method of identification is to store a serial number that identifies the object, and perhaps other information relating to the object or contents thereof, on a microchip that is attached to an antenna. The microchip and the antenna together are called an RFID transponder or an RFID tag. The antenna enables the microchip to transmit the identification information and other information to a RFID reader. The RFID reader converts the radio waves reflected back from the RFID tag into digital information that can then be passed on to computers that can make use of it.

As used herein, the expression "radio frequency identification system", or RFID system, comprises a RFID tag made up of a microchip with an antenna, and a RFID interrogator or RFID reader with an antenna. The RFID reader sends out electromagnetic waves. The tag antenna is tuned to receive these waves. A passive RFID tag draws power from the field created by the reader and uses it to power the circuits of the microchip. The microchip then modulates the waves that the passive RFID tag sends back to the RFID reader, which converts the waves received by the RFID reader into digital data.

As used herein, microchips in RFID tags can be "read-write microchips", "read-only microchips", or "write once, read many microchips." In the case of read-write microchips, information can be added to the RFID tag or existing information can be written over when the RFID tag is within range of a RFID reader. Read-write microchips usually have a serial number that cannot be written over. Additional blocks of data can be used to store additional information about the items to which the RFID tag is attached. These RFID tags can be locked to prevent overwriting of data or encrypted to prevent the disclosure of proprietary data or disclosure of data that would compromise the privacy of a patient. Read-only microchips have information stored on them during the manufacturing process. The information on them can never be changed. Write once, read many microchips have a serial number written to them once, and that information cannot be overwritten later.

As used herein, the expression "active RFID tags" have a transmitter and their own power source, typically a battery. The power source is used to run the microchip's circuitry and to broadcast a signal to a RFID reader. "Passive RFID tags" have no battery. Instead, passive RFID tags draw power from the RFID reader, which sends out electromagnetic waves that induce a current in the tag's antenna. "Semi-passive tags" use a battery to run the microchip's circuitry, but communicate by drawing power from the RFID reader. Any of the foregoing types of RFID tags can be used in the system of this invention.

As used herein, the expression "tag collision" occurs when more than one transponder reflects back a signal at the same time, confusing the RFID reader. Algorithms can be used to "singulate" the tags.

As used herein, the term "RFID reader" or "reader" means a device having the function of providing means for communicating with a RFID tag and facilitating transfer of data to and from a RFID tag. Functions performed by a RFID reader can include quite sophisticated signal conditioning, parity error checking, and correction. Once the signal from a RFID tag has been correctly received and decoded, algorithms can be applied to decide whether the signal is a repeat transmission, and can then instruct the RFID tag to cease transmitting. This type of interrogation is known as "command response protocol" and is used to circumvent the problem of reading a plurality of RFID tags in a short space of time. An alternative technique involves the RFID reader looking for RFID tags with specific identities, and interrogating them in turn. It is within the scope of this invention to use a single RFID reader or a plurality of RFID readers. A RFID reader can have a single antenna or a plurality of antennas.

Commercially available components suitable for use in the present invention are set forth in the following table:

TABLE I

| Item | Supplier | Model Number |
| --- | --- | --- |
| RFID reader | Escort Memory Systems (EMS), Scotts Valley, California | HF-0405-232-01 |
| Tags for containers for clinical chemistry analysis | Escort Memory Systems (EMS), Scotts Valley, California | HMS-112 |
| Tags for racks for holding sample containers | Escort Memory Systems (EMS), Scotts Valley, California | HMSP-108 |
| Tags for microplates | Escort Memory Systems (EMS), Scotts Valley, California | HMS-108 |
| Tags for containers for immunoassay analysis | Escort Memory Systems (EMS), Scotts Valley, California | LRP-P125 |
| Antenna extension | Escort Memory Systems (EMS), Scotts Valley, California | HF-0405-ANT-06 |
| Custom X-Y positioner for RFID reader | Parker Hannifin Corporation, Cleveland, Ohio | |
| Custom antenna board | Wavetrix, Inc. Richardson, Texas | |
| Microlab STARlet pipette (4 pipetting channels) | Hamilton Company, Reno, Nevada | 173000-001 |
| Hamilton Vector software | Hamilton Company, Reno, Nevada | |
| Hamilton labware:<br>(a) Multi-Flex Carrier Base with immunoassay, clinical chemistry, and microplate stackers<br>(b) 2 position holder for disposable tips<br>(c) 4 position holder for disposable tips<br>(d) Microplate core grippers<br>(e) bulk fluid troughs | Hamilton Company, Reno, Nevada | |

TABLE I-continued

| Item | Supplier | Model Number |
| --- | --- | --- |
| Custom method and liquid classes for processing immunoassays and clinical chemistry assays | Abbott Laboratories, Abbott Park, Illinois | |
| Custom labware: (a) immunoassay reagent storage rack with dispersing element (b) clinical chemistry reagent storage rack (c) microplate rotator with incubation control (d) sample carrier tray and racks | Abbott Laboratories, Abbott Park, Illinois | |
| Multi-axis motion controller | Pro-Dex Oregon Micro Systems, Beaverton, Oregon | MAXp-8000 |
| Motor driver | Intelligent Motion Systems, Marlborough, Connecticut | |
| Heater controllers; Heater pads and thermistors | Watlow Electric Manufacturing Company, St. Louis, Missouri | |

Radio frequency identification tags can be permanently applied to a given component, i.e., container, either by means of a molding process or by means of a bonding process. Radio frequency identification tags applied by molding or bonding are not re-usable. However, radio frequency identification tags can be rendered re-usable by ensuring that reagent containers, sample containers, or microplates are destroyed and the radio frequency identification tags recovered.

Reading radio frequency identification tags and writing radio frequency identification tags can be performed using ISO protocols 14443, 15693, or 18000, all of which are incorporated herein by reference, or combinations of the foregoing ISO protocols. These protocols utilize a three-layer communication model:

(a) application layer
(b) communication layer
(c) physical layer.

The three-layer communication model, primarily the communication layer, will provide the functions of error detection, error correction, identity authentication, collision avoidance, etc. These functions can be considered automatic, because they are part of the protocol for enabling the radio frequency identification reader to communicate with the radio frequency identification tag.

The application layer handles the information contained in the radio frequency identification tag. Such information can include at least some of the information in the following table:

TABLE II

| Class of data | Specific data |
| --- | --- |
| Tag identifier | Unique identifier for container |
| Manufacturing data | (a) Revision number(s) of reagent(s) (b) Serial number(s) of reagent(s) (c) Component identifier(s) (d) Component identifier(s) (e) Lot number(s) of reagent(s) (f) Stability/expiration data for reagent(s) (g) Times/dates of manufacture of reagent(s) (h) Configuration(s) of assay(s) (e.g., number of reagent containers needed) (i) Number of tests in container(s) (j) Associated components of assay(s) (k) Calibration data for assay(s) |

TABLE II-continued

| Class of data | Specific data |
| --- | --- |
| Shipping and storage data | (a) Temperature(s) of reagent during shipping (b) Times/dates of shipping movements and storage periods (c) Locations and dates of storage periods |
| Analyzer and usage data | (a) Times/dates of opening(s) of reagent container(s) (b) Number of aspirations from reagent container(s) (c) Carryover and potential contamination or dilution of reagent(s) or sample(s) (d) Encryption algorithms for protection of data (e) Other algorithms to ensure integrity of data |

The communication layer defines the manner whereby RFID readers and RFID tags communicate. The communication layer includes, but is not limited to, collision avoidance algorithms, parity checking algorithms, error-checking algorithms, and identification authentication algorithms. After the unique identifier of a RFID tag is known, a deterministic protocol can be used to ensure selectivity. The operation of a deterministic protocol is described, for example, in "RFID Traceability: A Multilayer Problem", Gildas Avoine and Philippe Oechslin, Ecole Polytechnique Federale De Lausanne, 2005, incorporated herein by reference.

The physical layer defines the actual interface and specifies at least the following: radio frequency (e.g., 13.56 MHz, 860 MHz, 960 MHz), modulation, data encoding, timing, etc.

The memory capacity of a radio frequency identification tag suitable for use in this invention typically ranges from about 112 to 736 bytes. This quantiy of bytes can exceed those in a typical barcode label. The radio frequency identification reader and other radio frequency identification tags (as specified in ISO 14443 or ISO 15693 or ISO 18000) can support memory capacity of up to 4000 bytes.

The operational details of the system of this invention can be controlled by computer. Furthermore, some higher level data integrity algorithms can be implemented. An example of a higher level data integrity algorithm is one that would indicate that reading the same radio frequency identification tag from multiple antennas is an error. Higher level algorithms suitable for use in this invention are known to those of ordinary skill in the art High selectivity requires close proximity of reader and radio frequency identification tags. In addition, use of metal or material exhibiting metal-like properties (such as carbon impregnated plastic), are preferably avoided in the system, because metal interferes with radio frequency identification signals.

Figure 1:
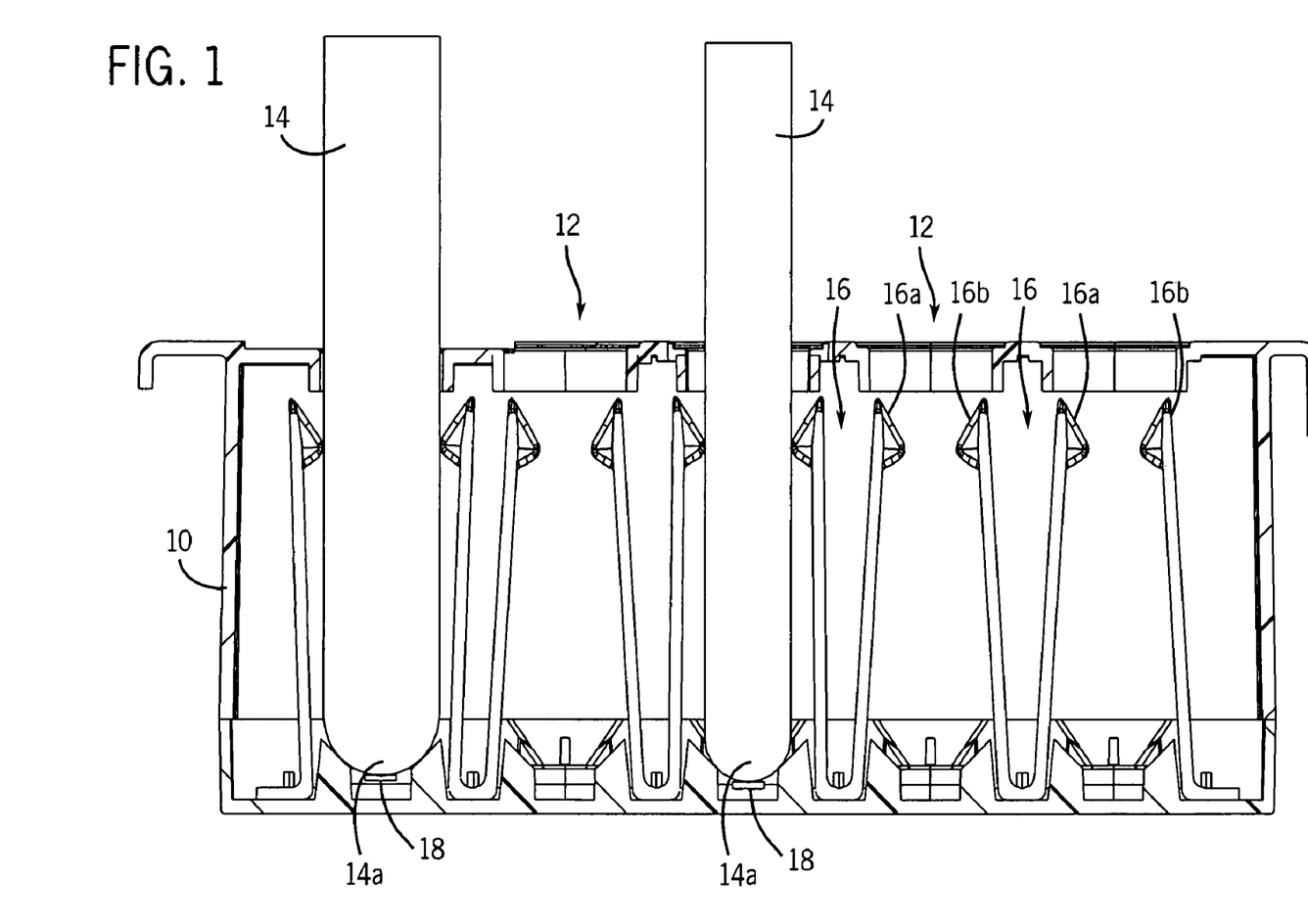
FIG. 1 is a cross-sectional view of a sample container carrier holding two sample containers, i.e., sample tubes. Radio frequency identification tags are attached to the lowermost ends of the sample tubes.

FIGS. 1-7 illustrate various embodiments of reagent containers, sample containers, transmission sub-systems for RFID readers, and printed circuit boards containing a plurality of RFID readers. FIG. 1 illustrates where radio frequency identification tags can be attached to sample containers. Referring now to FIG. 1, a rack 10 has a plurality of slots 12 for holding sample containers 14, e.g., test tubes. Each slot 12 is separated from the adjacent slot by a resilient gripping device 16. Each resilient gripping device 16 comprises a tube gripper 16a and a tube gripper 16b. The resilient gripping devices 16 are positioned so that the gripper 16a of one gripping device 16 faces the gripper 16b of an adjacent gripping device 16. A sample container 14 is inserted between the gripper 16a of one gripping device 16 and the gripper 16b of an adjacent gripping device 16 to securely hold the sample container, i.e., test tube in an upright manner. Each resilient gripping device is typically constructed from a resilient material, such as, for example, resilient polymeric material. In FIG. 1, the sample container 14 is in the form of a tube. Each radio frequency identification tag 18 is attached at the lowermost end 14a of each sample container 14 and is read from underneath the container 14 by an RFID reader (not shown). The system should be able to identify and track a sample by radio frequency identification tag (constructed in accordance with ISO 14443 or ISO 15693 or ISO 18000) attached to the sample container. As mentioned earlier, radio frequency identification provides the ability to aggregate read information related to a sample in addition to the sample identifier. Information can include (a) demographics of a patient, (b) the date the sample was obtained, (c) the test(s) to be performed on the sample, (d) the type of sample, (e) the type of container, etc. Radio frequency identification can also be used to track shipping and storage conditions that may affect integrity of the sample. In addition, radio frequency identification can be used for writing information such as, for example, centrifugation performed on the sample, aspiration operations performed, potential contamination or dilution of a sample by material carried over by the tip of an aspirating device, freeze-thaw history of the sample, etc. Radio frequency identification also provides the ability to positively verify a sample identifier during aspiration or dispensing, thereby enabling an operator of the system to be given physical access to samples and reagents, except for those samples and reagents currently being aspirated or dispensed. Physical access to samples or reagents currently being aspirated or dispensed should be prohibited to the operator in order to ensure the safety of the operator.

Figure 2:
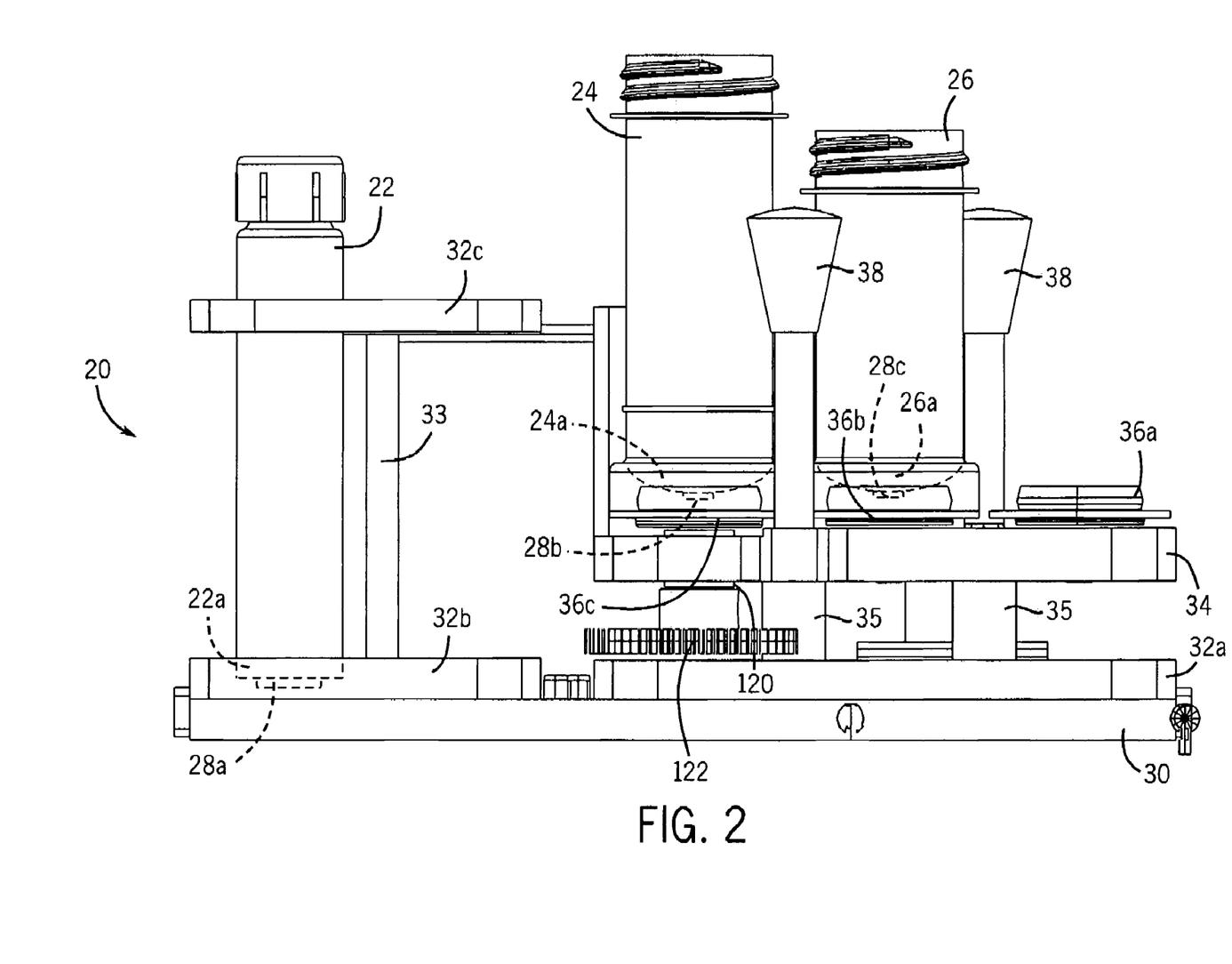
FIG. 2 is a side view in elevation showing a reagent container carrier holding three reagent containers. Radio frequency identification tags are attached to the lowermost ends of the reagent containers. The contents of one of the reagent containers shown are used in clinical chemistry assays. The contents of two of the reagent containers shown are used in immunoassays.

FIG. 2 illustrates where radio frequency identification tags can be attached to reagent containers. Referring now to FIG. 2, a reagent container holder 20 holds a plurality of reagent containers 22, 24, and 26. In FIG. 2, the reagent container 22 is in the form of a cylindrical bottle having a flat bottom. The reagent container 22 can be used for reagents for clinical chemistry assays. The reagent containers 24 and 26 are in the form of cylindrical bottles having rounded bottoms. The reagent containers 24 and 26 can be used for reagents for immunoassays. The reagent container 26 is of lesser height than the reagent container 24. The lowermost end of container 22 is designated by the reference numeral 22a; the lowermost end of container 24 is designated by the reference numeral 24a; the lowermost end of container 26 is designated by the reference numeral 26a. Radio frequency identification tags 28a, 28b, and 28c are attached at the lowermost end 22a of container 22, the lowermost end 24a of container 24, and the lowermost end 26a of container 26, respectively, and are read from underneath the reagent containers 22, 24, and 26 by an RFID reader (not shown). In FIG. 2, the reagent containers 22, 24, and 26 are supported by and held by a sub-system comprising a locking, or adapter, plate 30, a base 32a, a holder comprising a lower portion 32b and an upper portion 32c, a vertical support 33 for supporting the upper portion 32c, a platform 34 upon which reagent containers can be mounted, at least one vertical support 35 for the platform 34, seats 36a, 36b, and 36c, and lifting handles 38. The seats 36a, 36b, and 36c are constructed so as to enable reagent containers for reagents for immunoassays to be securely, but removably, fastened to the platform 34 of the sub-system shown in FIG. 2. The lower portion 32b and the upper portion 32c of the holder have apertures (not shown) formed therein. These apertures are of such dimensions that a reagerit container for reagents for clinical chemistry assays can be securely, but removably, inserted therein. The base 32a is an intermediate element that connects the platform 34 to the locking plate 30 via the at least one support 35. The lifting handles 38 have the function of providing a means for introducing and removing the sub-system holding the reagent containers from the storing and staging system shown in FIG. 4. The locking plate 30 has the function of securing the base 32a and the lower portion 32b of the holder to the storing and staging system shown in FIG. 4.

The system should be able to identify and track a reagent by radio frequency identification tag (constructed in accordance with ISO 14443 or ISO 15693 or ISO 18000) attached to the reagent container. As mentioned earlier, radio frequency identification provides the ability to aggregate read information related to the reagent in addition to the reagent identifier. Information can include calibration data, lot number of the reagent, serial number of the reagent, component identifier, assay identifier, expiration date of the reagent, kit size, package insert information, etc. Radio frequency identification can also be used to track shipping and storage conditions that may affect the integrity of the reagent. In addition, radio frequency identification can be used for writing information such as test count remaining, on-board expiration date (after the container has been opened), aspiration operations performed, potential contamination or dilution of a sample by material carried over by the tip of an aspirating device, etc. Radio frequency identification also provides the ability to positively verify a reagent identifier during aspiration or dispensing, thereby enabling an operator of the system to be given physical access to samples and reagents, except for those samples and reagents currently being aspirated or dispensed. Physical access to samples or reagents currently being aspirated or dispensed should be prohibited to the operator in order to ensure the safety of the operator.

Figure 3:
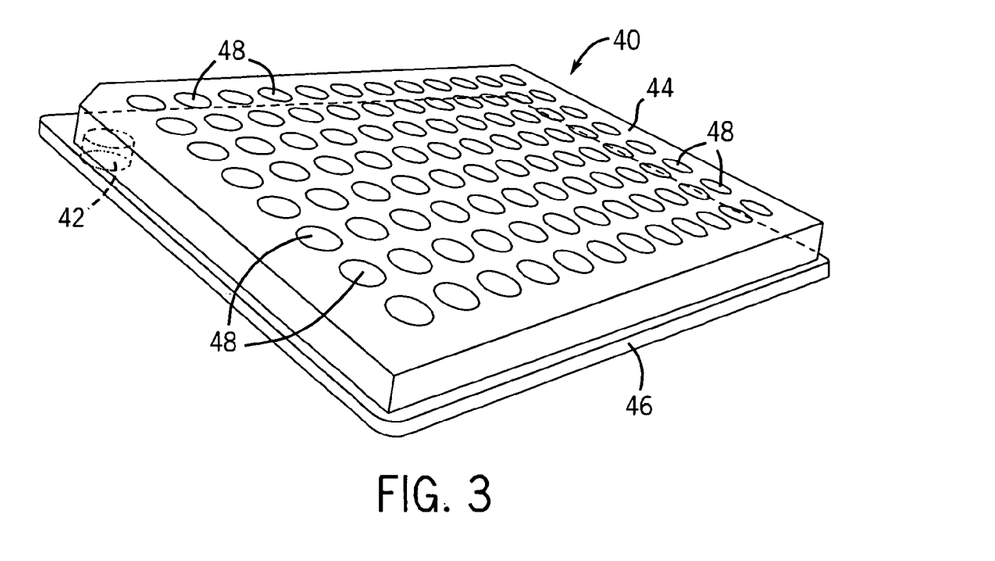
FIG. 3 is a perspective view showing a microplate. A radio frequency identification tag is attached to the base of the microplate.

FIG. 3 illustrates attachment of radio frequency identification tags to microplates. Microplates are described in greater detail in U.S. Pat. No. 4,735,778 and in U.S. Patent Application Publication 2005/0242963, both of which are incorporated herein by reference. FIG. 7 of U.S. Patent Application Publication 2005/0242963 shows a microplate having a structure similar to that of the microplate 40 shown in FIG. 3 herein. A radio frequency identification tag 42, shown in phantom, is associated with the microplate 40. In FIG. 3, the microplate 40 has an upper portion 44 attached to a base 46.

A plurality of wells 48 is formed in the upper portion 44 of the microplate 40. The upper portion 44 of the microplate 40 rests on the base 46. The radio frequency identification tag 42 is attached to the base 46. The radio frequency identification tag 42 is embedded within a portion of the microplate 40. In an alternative embodiment, the radio frequency identification tag can be applied to an exterior surface of the microplate. Any microplate having 8, 16, 24, 48, 96, 384, 768, 1536, etc., wells is contemplated for use in with the invention described herein. The radio frequency identification tag 42 can be read from underneath the microplate 40. Because the distance between the radio frequency identification reader and radio frequency identification tag is small, the placement of the radio frequency identification tag 42 also indicates the physical orientation of the microplate 40. For example, if the radio frequency identification tag 42 is always located adjacent to the A1 position on the microplate 40, reading the radio frequency identification tag 42 ensures that the microplate 40 is oriented with position A1 over the RFID reader (i.e., the position at the upper left hand corner of the microplate). The system should be able to identify and track a microplate by the radio frequency identification tag (as constructed in accordance with ISO 14443 or ISO 15693 or ISO 18000) on the microplate. Radio frequency identification provides the ability to aggregate read information related to the assay steps, such as, for example, loading, dispensing, and the reagents in the microplate, in addition to the microplate identifier. Information can include lot number of the microplate, serial number of the microplate, expiration date of the microplate, etc. Radio frequency identification can also be used to track shipping and storage conditions that may affect integrity of the microplate. In addition, radio frequency identification can be used for writing information such as date used, on-board expiration date (after the container has been opened), etc.

Figure 4:
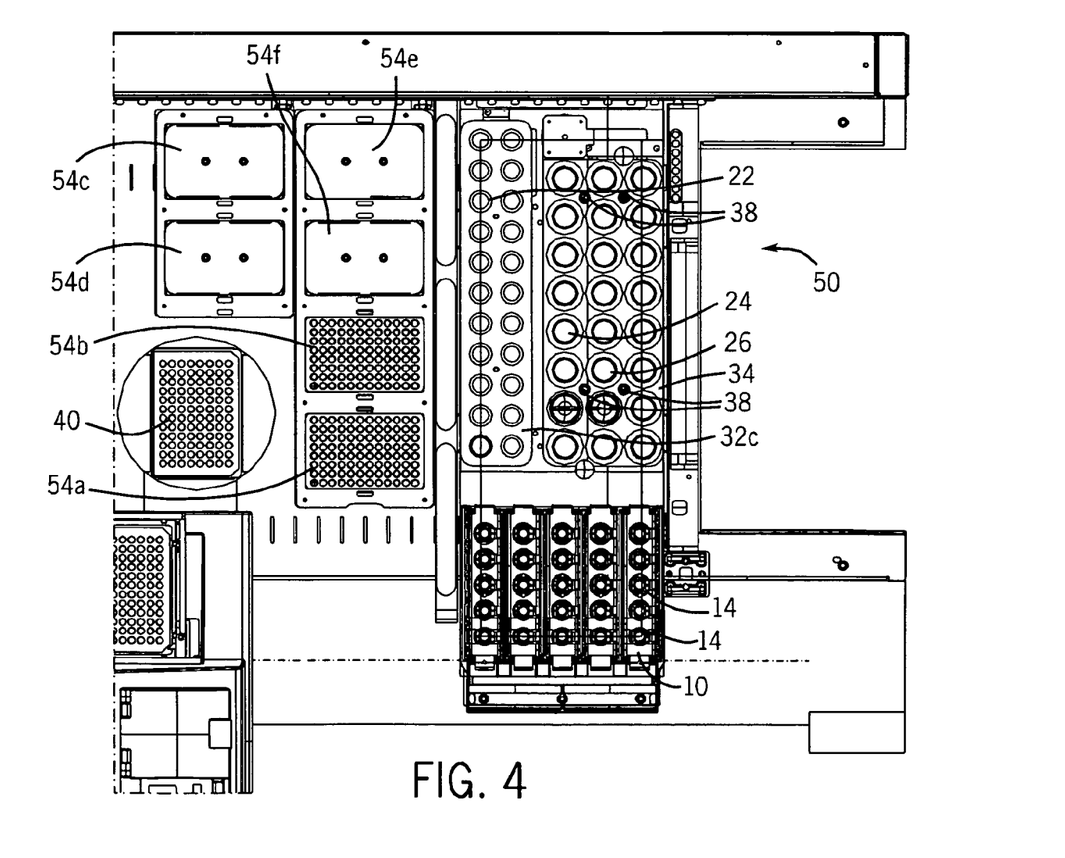
FIG. 4 is a top plan view of a portion of an area of a system for storing and staging sample containers of the type shown in FIG. 1, reagent containers of the type shown in FIG. 2, and microplates of the type shown in FIG. 3.

FIG. 4 illustrates a storage area/staging area 50 for reagents, samples, and other supplies. The storage area/staging area 50 provides positions for the sample containers shown in FIG. 1, the reagent containers shown in FIG. 2, and the microplates shown in FIG. 3. A microplate 40 is shown in position at the left side of the view of the storage -area/staging area 50. Reagent containers 22 containing reagents for clinical chemistry assays are positioned in the apertures (not shown) in upper portion 32c and lower portion 32b of the holder, as illustrated in greater detail in FIG. 2. The reagent containers 24 and 26 containing reagents for immunoassays are positioned in the seats 36c and 36b, respectively, as illustrated in greater detail in FIG. 2. Sample containers 14 containing biological samples are positioned in the slots 12 of the rack 10, as illustrated in greater detail in FIG. 1. Disposable tip holders 54a and 54b are located adjacent to the microplate 52. Additional locations for disposable tip holders are designated at 54c, 54d, 54e, and 54f. The radio frequency identification tags can be read at various positions beneath the storage area 50.

Figure 5:
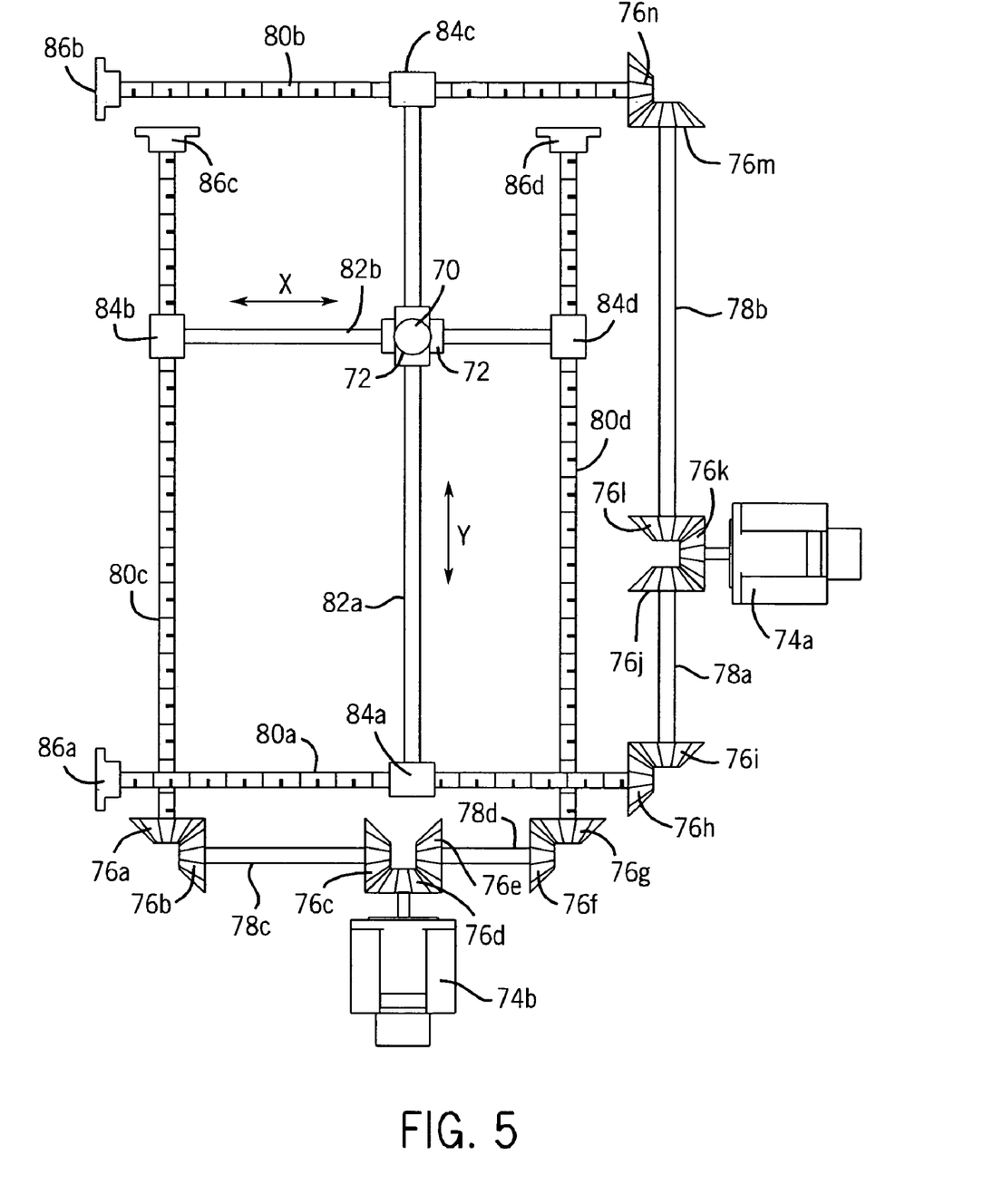
FIG. 5 is a top plan view of a transmission system comprising stepper motors, gears, gear shafts, lead screws, and movable rods. The system shown is capable of moving a radio frequency identification reader mounted on a carriage in two directions in a plane.
Figure 6:
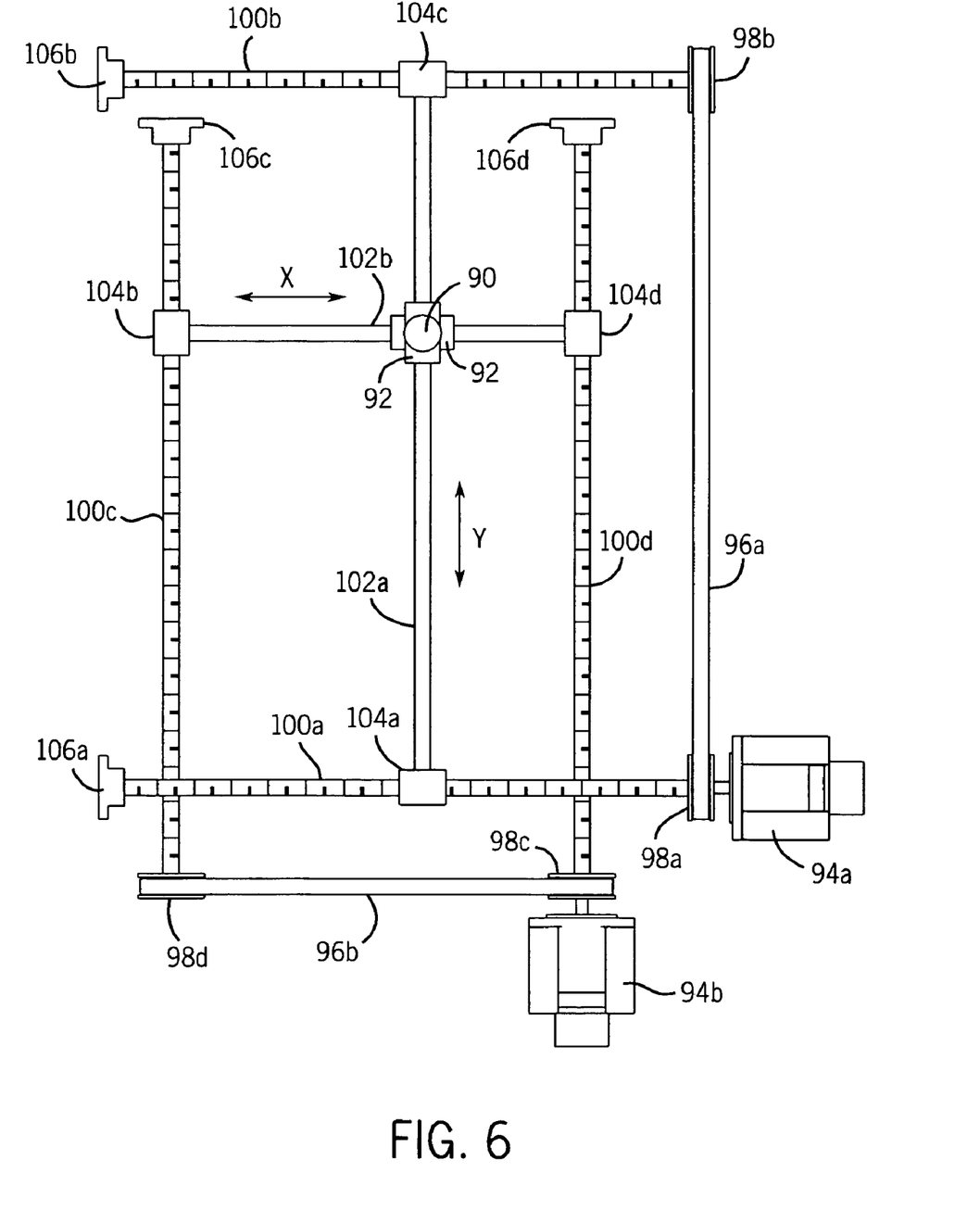
FIG. 6 is a top plan view of a system comprising stepper motors, drive belts, pulleys, lead screws, and movable rods. The system shown is capable of moving a radio frequency identification reader mounted on a carriage in two directions in a plane.

FIGS. 5 and 6 illustrate systems for movement of radio frequency identification reader heads for reading radio frequency identification tags. In FIG. 5, a radio frequency identification reader head 70 mounted on a X-Y bearing carriage 72 can be moved in a direction parallel to the X-axis and in a direction parallel to the Y-axis by a transmission system comprising motors 74a and 74b, gears 76a, 76b, 76c, 76d, 76e, 76f, 76g, 76h, 76i, 76j, 76k, 76l, 76m, and 76n, gear shafts 78a, 78b, 78c, and 78d, lead screws 80a, 80b, 80c, and 80d, and movable rods 82a and 82b. The lead screws 80a, 80b, 80c, and 80d are threaded. The movable rods 82a and 82b are not threaded. As shown in FIG. 5, the gears are bevel gears, but other types of gears can also be used. Nuts 84a and 84c function to enable the X-Y bearing carriage 72 bearing the radio frequency identification reader head 70 to move with movable rod 82a in a direction parallel to the X-axis when the lead screws 80a and 80b are caused to rotate by the transmission system. Nuts 84b and 84d function to enable X-Y bearing carriage 72 bearing the radio frequency identification reader head 70 to move with movable rod 82b in a direction parallel to the Y-axis when the lead screws 80c and 80d are caused to rotate by the transmission system. The nuts 84a, 84b, 84c, and 84d are threaded to enable them to move upon the threads of the lead screws 80a, 80b, 80c, and 80d when required and to remain immobile in their proper positions on the lead screws 80a, 80b, 80c, and 80d when required. Bearings 86a, 86b, 86c, and 86d function to support, guide, and reduce the friction of the lead screws 80a, 80b, 80c, and 80d, respectively. As shown in FIG. 5, the lead screws 80a and 80b and the movable rod 82a for moving the X-Y bearing carriage 72 bearing the radio frequency identification reader head 70 in a direction parallel to the X-axis are positioned above the lead screws 80c and 80d and the movable rod 82b for moving the X-Y bearing carriage 72 bearing the radio frequency identification reader head 70 in a direction parallel to the Y-axis.

In order to the X-Y bearing carriage 72 bearing the radio frequency identification reader head 70 in a direction parallel to the X-axis, the motor 74a is activated. The motor 74a can be a stepper motor. The shaft of the motor 74a causes the gear 76k to rotate; the rotating gear 76k causes the gears 76j and 76l to rotate. The rotation of the gears 76j and 76l causes the gear shafts 78a and 78b, respectively, to rotate. The rotation of the gear shafts 78a and 78b causes the rotation of the gears 76i and 76m, respectively. The rotation of the gears 76i and 76m causes the gears 76h and 76n, respectively, to rotate. The rotation of the gears 76h and 76n causes the lead screws 80a and 80b to rotate, thereby causing the nuts 84a and 84c, which support the movable rod 82a, to move the X-Y bearing carriage 72 bearing radio frequency identification reader head 70 in a direction parallel to the X-axis. In order to move the X-Y bearing carriage 72 bearing the radio frequency identification reader head 70 in a direction parallel to the Y-axis, the motor 74b is activated. The motor 74b can be a stepper motor. The shaft of the motor 74b causes the gear 76d to rotate; the rotating gear 7dk causes the gears 76c and 76e to rotate. The rotation of the gears 76c and 76e causes the gear shafts 78c and 78d, respectively, to rotate. The rotation of the gear shafts 78c and 78d causes the rotation of the gears 76b and 76f, respectively. The rotation of the gears 76b and 76f causes the gears 76a and 76g, respectively, to rotate. The rotation of the gears 76a and 76g causes the lead screws 80c and 80d to rotate, thereby causing the nuts 84b and 84d, which support the movable rod 82b, to move the move the X-Y bearing carriage 72 bearing the radio frequency identification reader head 70 in a direction parallel to the Y-axis. By appropriate movement of the X-Y bearing carriage 72 bearing the radio frequency identification reader head 70 in directions parallel to the X-axis and the Y-axis, the radio frequency identification reader head 70 can be positioned so as to enable the radio frequency identification reader head 70 to read the desired radio frequency identification tag.

In FIG. 6, a radio frequency identification reader head 90 mounted on a X-Y bearing carriage 92 can be moved in a direction parallel to the X-axis and in a direction parallel to the Y-axis by a transmission system comprising stepper motors 94a and 94b, drive belts 96a, 96b, pulleys 98a, 98b, 98c, and 98d, lead screws 100a, 100b, 100c, and 100d, and movable rods 102a and 102b. The lead screws 100a, 100b, 100c, and 100d are threaded. The movable rods 102a and 102b are not threaded. Nuts 104a and 104c function to enable the X-Y bearing carriage 92 bearing the radio frequency identification reader head 90 to move with movable rod 102a in a direction parallel to the X-axis when the lead screws 100a and 100b are caused to rotate by the transmission system. Nuts 104b and 104d function to enable the X-Y bearing carriage 92 bearing the radio frequency identification reader head 90 to move with movable rod 102b in a direction parallel to the Y-axis when the lead screws 100c and 100d are caused to rotate by the transmission system. The nuts 104a, 104b, 104c, and 104d are threaded to enable them to move upon the threads of the lead screws 100a, 100b, 100c, and 100d when required and to remain immobile in their proper positions on the lead screws 100a, 100b, 100c, and 100d when required. Bearings 106a, 106b, 106c, and 106d function to support, guide, and reduce the friction of the lead screws 100a, 100b, 100c, and 100d, respectively. As shown in FIG. 6, the lead screws 100a, 100b, and the movable rod 102a for moving the X-Y bearing carriage 92 bearing radio frequency identification reader head 90 in a direction parallel to the X-axis are positioned above the lead screws 100c, 100d, and the movable rod 102b for moving the X-Y bearing carriage 92 bearing the radio frequency identification reader head 90 in a direction parallel to the Y-axis.

In order to move the X-Y bearing carriage 92 bearing the radio frequency identification reader head 90 in a direction parallel to the X-axis, the motor 94a is activated. The motor 94a can be a stepper motor. The shaft of the motor 94a drives the pulley 98a, thereby driving the drive belt 96a, which moves over the pulleys 98a and 98b, thereby causing the lead screws 100a and 100b to rotate, which, in turn, causes the nuts 104a and 104c, which support the movable rod 102a, to move the X-Y bearing carriage 92 bearing the radio frequency identification reader head 90 in a direction parallel to the X-axis. In order to move the X-Y bearing carriage 92 bearing the radio frequency identification reader head 90 in a direction parallel to the Y-axis, the motor 94b is activated. The motor 94b can be a stepper motor. The shaft of the motor 94b drives the pulley 98c, thereby driving the drive belt 96b, which moves over the pulleys 98c and 98d, thereby causing the lead screws 100c and 100d to rotate, which, in turn, causes the nuts 104b and 104d, which support the movable rod 102b to move the X-Y bearing carriage 92 bearing the radio frequency identification reader head 90 in a direction parallel to the Y-axis. By appropriate movement of the X-Y bearing carriage 92 bearing the radio frequency identification reader head 90 in directions parallel to the X-axis and the Y-axis, the radio frequency identification reader head 90 can be positioned so as to enable the radio frequency identification reader head 90 to read the desired radio frequency identification tag.

Figure 7:
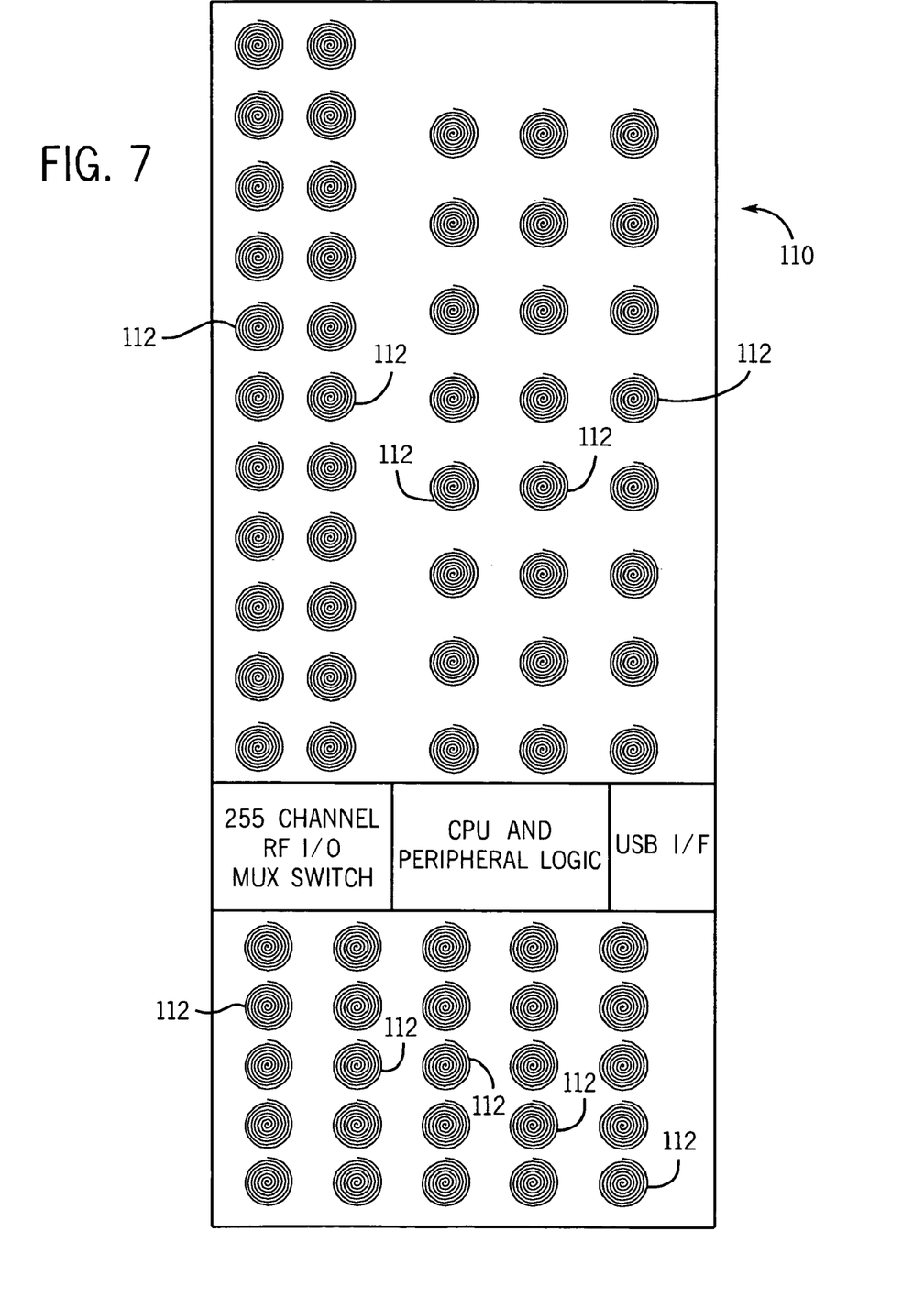
FIG. 7 is a top plan view of a printed circuit board having an array of radio frequency identification reader antennas. The printed circuit board shown in FIG. 7 can be used with the portion of the area of the system shown in FIG. 4.

In FIG. 7, a printed circuit board 110 contains a plurality of radio frequency identification reader antennas 112. Each antenna 112 is selectively activated by means of electronics. In FIG. 7, the 5×5 array of antennas at the lower portion of the printed circuit board 110 corresponds to the portion of the storage area/staging area 50 of FIG. 4 where the sample containers 14 are located. The 3×8 array of antennas at the upper right portion of the printed circuit board 110 corresponds to the portion of the storage area/staging area 50 of FIG. 4 where the reagent containers 24 and 26 containing reagents for immunoassays are located. The 2×11 array of antennas at the upper left portion of the printed circuit board 110 corresponds to the portion of the storage area/staging area 50 of FIG. 4 where the reagent containers 22 containing reagents for clinical chemistry assays are located. A large printed circuit board containing a plurality of antennas, such as that shown in FIG. 7, eliminates the need to move a reader head by means of the type of mechanisms shown in FIGS. 5 and 6. Through the use of a large printed circuit board containing a plurality of antennas, such as that shown in FIG. 7, signals from the RFID tags attached to containers can be read by stationary antennas 112 for further processing by a RFID reader associated with the antennas 112. It is also within the scope of this invention to employ a plurality of RFID readers with a printed circuit board of the type shown in FIG. 7.

In order for signals to be transmitted between an antenna of a RFID tag and the antenna of a RFID reader, there must be an antenna aperture between the antenna of the RFID tag and the antenna of the RFID reader. Referring now to FIG. 2, the bearings (not shown), the dispersion spindle, which is designated by the reference numeral 120 in FIG. 2, and the gear for rotating the dispersion spindle, which is designated by the reference numeral 122 in FIG. 2, should be transparent to the signals transmitted between the antenna of the RFID tag and the antenna of the RFID reader. The bearings, the dispersion spindle, and the gear are preferably made from a polymeric material. The materials of the barrier that is not in the path of the signals transmitted between the antenna of the RFID tag and the antenna of the RFID reader can be formed from a metallic material or carbon impregnated plastic. This barrier is designated by the reference numeral 30. By the use of appropriate materials, antenna apertures can be constructed to provide adequate sensitivity as well as selectivity. After a prototype printed circuit board containing a plurality of antennas board has been completed, testing may indicate that additional shaping techniques for antenna apertures should be employed. Additional metal, or other materials exhibiting metal-like properties, can be employed in various geometric shapes to enhance selectivity and propagation of radio frequency waves. It is expected that as new techniques become available to reduce cost of radio frequency identification tags, such techniques will be employed.

Smaller radio frequency identification tag antennas can be used to decrease reading range, increase selectivity, and provide physical orientation performance, but such antennas require closer proximity of the radio frequency identification tag to the radio frequency identification reader.

According to the systems of this invention, radio frequency identification tags can be selectively read at each position of a reagent container or at each position of a sample container, e.g., a sample tube, from a point below the reagent container or sample container. Because the distance of the radio frequency identification tag from the radio frequency identification reader is typically small, e.g., less than 1 inch, and the antenna aperture limits side lobes, the placement of the radio frequency identification tag can also provide information relating to the type of analyzer and the type of container, thereby providing (a) improved functioning of automated analyzer(s) in a system, (b) improved chain of custody, i.e., improved information relating to locations occupied by a given container in the present and at times previous to the present, and (c) improved safety to patients by ensuring accurate results of assays.

Operation

Radio frequency identification tags can be either attached to or molded into a container, such as, for example, a reagent container, a sample container, e.g., a sample tube, a microplate, and the like. Initial manufacturing information is typically programmed into radio frequency identification tags. Storage and shipping information (e.g., logistics) are typically concatenated to previous data in radio frequency identification tags.

Radio frequency identification tags on reagent containers, sample containers, and microplates, and the like, are read when placed on the radio frequency identification system of this invention. Objects bearing radio frequency identification tags can be moved to a position in close proximity to a radio frequency identification reader. Alternatively, an object bearing a radio frequency identification tag can be read in place by moving a radio frequency identification reader to a position in close proximity to the radio frequency identification tag. In still another alternative, a plurality of antennas associated with a radio frequency identification reader can be used in lieu of a movable radio frequency identification reader. One or more antennas of containers can be selected, and then information in the radio frequency identification tags of these containers can be read. Information and physical locations of reagent containers, sample containers, and the like, can be substantiated.

As the contents of the reagent containers, sample containers, microplates, etc. are accessed and the contents are consumed during the performance of an assay, additional information can be concatenated to previous data in radio frequency identification tags. A large printed circuit board containing a plurality of antennas, such as the type shown in FIG. 7, eliminates the need to move an antenna having a mechanism of the type shown in FIGS. 5 and 6.

The power of the radio frequency identification reader is limited to 4 watts EIRP. In the systems described herein, the planes of the radio frequency identification reader antennas and radio frequency identification tag antennas are preferably parallel to each other, and, when being read, the center of each radio frequency identification tag antenna is preferably positioned over the center of the radio frequency identification reader antenna. The distance from the radio frequency identification reader to the radio frequency identification tag typically ranges from about 0.100 inch to about 1.25 inches.

Radio frequency identification can be used to enhance information on the containers for reagents, containers for samples, microplates, and the like, so that the information can be directly linked to a database and provide (a) improved functioning of automated analyzer(s) in a system, (b) improved chain of custody, i.e., improved information relating to locations occupied by a given container in the present and at times previous to the present, and (c) improved safety to patients by ensuring accurate results of assays. This information includes, but is not limited to, information related to the automated analyzer, information related to the environments experienced during shipping, storage, and usage of the contents of the containers, and information related to the containers.

Because RFID tags can be read at a processing location (i.e., an aspiration location, a dispensing location, etc.), physical access for an operator to samples and reagents, except for those samples and reagents currently being aspirated or dispensed, can be increased. However, physical access to samples or reagents currently being aspirated or dispensed should be prohibited to the operator in order to ensure the safety of the operator.

Automated analyzers that can be used with the radio frequency identification system of this invention include, but are not limited to, automated immunoassay instruments, automated clinical chemistry instruments, automated hematology instruments, automated nucleic acid analyzer instruments, such as, for example, automated nucleic acid microarray analyzer instruments and an automated nucleic acid amplification analyzer instrument, automated slide processing instruments, and automated protein analyzer instruments. Of course, the aforementioned instruments will include the sub-systems required to enable operation thereof, such as, for example, immunoassay readers, clinical chemistry readers, software, fluid transfer mechanisms, etc. The automated analyzers that can be used with the radio frequency identification instruments can further include an automated sample processing station, such as, for example, an apparatus for extraction of nucleic acid from a biological sample. It is also possible for the system of this invention to have a plurality of analysis stations, wherein each of the plurality of analysis stations comprises apparatus for the automated analysis of a biological sample. The analysis stations can employ analyzers from list of analyzers mentioned previously. In addition, in certain embodiments the system of this invention can further comprise an automated sample processing station.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A system comprising a plurality of containers, each of which container has a top and a bottom and contains a liquid, each of which container has a radio frequency identification tag attached thereto on the bottom thereof, the system further including at least one movable radio frequency identification reader, wherein the movable radio frequency identification reader is movable to a position below the radio frequency identification tag, whereby information from the radio frequency identification tag is read with an amount of noise and interference from nearby radio frequency identification tags on other containers insufficient to adversely affect the integrity of the data read by a radio frequency identification reader.

2. The system of claim 1, further including a transmission sub-system for enabling the at least one reader to move within the system.

3. The system of claim 1, further including at least one analysis station comprising apparatus for automated analysis of a biological sample from a patient.

4. The system of claim 3, wherein the at least one container is transportable to a location in the system, and said system further includes a sub-system for tracking the location of the at least one container in the system.

5. The system of claim 3, wherein the at least one analysis station comprises an automated immunoassay instrument.

6. The system of claim 3, wherein the at least one analysis station comprises an automated clinical chemistry instrument.

7. The system of claim 3, wherein the at least one analysis station comprises an automated hematology instrument.

8. The system of claim 3, wherein the at least one analysis station comprises an automated nucleic acid analyzer instrument.

9. The system of claim 8, wherein the automated nucleic acid analyzer instrument is selected from the group consisting of an automated nucleic acid microarray analyzer instrument and an automated nucleic acid amplification analyzer instrument.

10. The system of claim 3, wherein the at least one analysis station comprises an automated slide processing instrument.

11. The system of claim 3, wherein the at least one analysis station comprises an automated protein analyzer instrument.

12. The system of claim 3, further comprising an automated sample processing station.

13. The system of claim 12, wherein the automated sample processing station comprises apparatus for extraction of nucleic acid from a biological sample.

14. The system of claim 3, comprising a plurality of analysis stations, wherein each of said plurality of analysis stations comprises apparatus for the automated analysis of a biological sample.

15. The system of claim 14, comprising at least two analysis stations, wherein said at least two analysis stations are selected from the group consisting of automated immunoassay instruments, automated hematology instruments, automated nucleic acid analyzer instruments, automated slide processing instruments, and automated protein analyzer instruments.

16. The system of claim 15, further comprising an automated sample processing station.

17. A system comprising a plurality of containers, each of which container has a top and a bottom and contains a liquid, each of which container has a radio frequency identification tag attached thereto on the bottom thereof, the system further including at least one radio frequency identification reader, said at least one radio frequency identification reader having a plurality of stationary antennas, wherein each of the plurality of containers is movable to a position above one of the plurality of radio frequency identification antennas of the at least one radio frequency identification reader, whereby information from the radio frequency identification tag is read with an amount of noise and interference from nearby radio frequency identification tags on other containers insufficient to adversely affect the integrity of the data read by an antenna of said at least one radio frequency identification.

18. The system of claim 17, wherein each of said plurality of stationary radio frequency identification antennas of said radio frequency identification reader is a trace on a printed circuit board.

19. The system of claim 17, wherein each radio frequency identification tag has an antenna having a length, the length of each antenna determining the relationship with the radio frequency used.

20. The system of claim 17, wherein the radio frequency identification tags are encapsulated.

21. The system of claim 17, wherein the antennas of the antennas of the at least one radio frequency identification reader are positioned in an array characterized by Cartesian coordinates.

22. The system of claim 17, further including at least one analysis station comprising apparatus for automated analysis of a biological sample from a patient.

23. The system of claim 22, wherein the at least one container is transportable to a location in the system, and said system further includes a sub-system for tracking the location of the at least one container in the system.

24. The system of claim 22, wherein the at least one analysis station comprises an automated immunoassay instrument.

25. The system of claim 22, wherein the at least one analysis station comprises an automated clinical chemistry instrument.

26. The system of claim 22, wherein the at least one analysis station comprises an automated hematology instrument.

27. The system of claim 22, wherein the at least one analysis station comprises an automated nucleic acid analyzer instrument.

28. The system of claim 27, wherein the automated nucleic acid analyzer instrument is selected from the group consisting of an automated nucleic acid microarray analyzer instrument and an automated nucleic acid amplification analyzer instrument.

29. The system of claim 22, wherein the at least one analysis station comprises an automated slide processing instrument.

30. The system of claim 22, wherein the at least one analysis station comprises an automated protein analyzer instrument.

31. The system of claim 22, further comprising an automated sample processing station.

32. The system of claim 31, wherein the automated sample processing station comprises apparatus for extraction of nucleic acid from a biological sample.

33. The system of claim 22, comprising a plurality of analysis stations, wherein each of said plurality of analysis stations comprises apparatus for the automated analysis of a biological sample.

34. The system of claim 33, comprising at least two analysis stations, wherein said at least two analysis stations are selected from the group consisting of automated immunoassay instruments, automated hematology instruments, automated nucleic acid analyzer instruments, automated slide processing instruments, and automated protein analyzer instruments.

35. The system of claim 34, further comprising an automated sample processing station.

36. A method of determining whether a biological sample is acceptable for the analysis thereof in a system comprising an automated analyzer, the method comprising the steps of:
(a) providing a liquid biological sample in a container having a top and a bottom, the radio frequency identification tag positioned on the bottom of the container;
(b) interrogating a radio frequency identification tag on said container containing said liquid biological sample to obtain information therefrom relating to storage information wherein said radio frequency identification tag is interrogated by a radio frequency identification reader, wherein said radio frequency identification reader is in a position below the container so that information from the radio frequency identification tag is read with an amount of noise and interference from nearby radio frequency identification tags on other containers that are insufficient to adversely affect the integrity of the data read by the radio frequency identification reader;
(c) comparing the storage information to a set of acceptable storage conditions; and
(d) rejecting or accepting the sample container for analysis of the sample, based on the comparing step performed in (c),
wherein steps (b), (c) and (d) are automatically performed by an automated analyzer system.

37. The method of claim 36, further comprising the step of performing at least one analysis of the biological sample.

38. The method of claim 37, wherein the analysis is performed with at least one instrument selected from the group consisting of automated immunoassay instruments, automated clinical chemistry instruments, automated hematology instruments, automated nucleic acid analyzer instruments, automated slide processing instruments, and automated protein analyzer instruments.

39. The method of claim 36, further comprising updating an information database to specify the location of each sample container present in the automated analyzer system.

40. The method of claim 36, further comprising updating the information database to specify the quantity of liquid removed from each sample container present in the automated analyzer system.

41. A method of determining whether a reagent is acceptable for the analysis of a biological sample in an automated analyzer system, the method comprising the steps of:
(a) providing a liquid reagent in a container having a top and a bottom, a radio frequency identification tag attached to the bottom of the container, wherein the radio frequency identification tag comprises an information device that contains information on storage conditions to which the reagent container has been exposed;

(b) interrogating a radio frequency identification tag on said container containing said liquid reagent to determine the information on storage conditions for the at least one reagent container wherein said radio frequency identification tag is interrogated by a radio frequency identification reader, wherein said radio frequency identification reader is in a position below the container so that information from the radio frequency identification tag is read with an amount of noise and interference from nearby radio frequency identification tags on other containers that are insufficient to adversely affect the integrity of the data read by the radio frequency identification reader;

(c) comparing the information on storage conditions to a set of acceptable storage conditions; and (d) rejecting or accepting the reagent container for use in an automated analyzer system, based on the comparing step performed in step (c), wherein steps (b), (c) and (d) are automatically performed by an automated analyzer system.

42. The method of 41, further comprising the step of performing at least one automated analysis of the sample using at least one reagent container determined to be acceptable for use.

43. The method of claim 41, wherein the automated analysis is performed with at least one instrument selected from the group consisting of automated immunoassay instruments, automated clinical chemistry instruments, automated hematology instruments, automated nucleic acid analyzer instruments, automated slide processing instruments, and automated protein analyzer instruments.

44. The method of claim 41, further comprising the step of updating an information database to specify location of each reagent container present in the automated analyzer system.

45. The method of claim 41, further comprising the step of updating an information database to specify the quantity of sample removed from each sample container present in the automated analyzer system.

* * * * *